(12) United States Patent
Takahashi et al.

(10) Patent No.: US 11,460,456 B2
(45) Date of Patent: Oct. 4, 2022

(54) GAS SENSOR

(71) Applicant: NGK INSULATORS, LTD., Aichi (JP)

(72) Inventors: Fumiya Takahashi, Nagoya (JP); Takeshi Omori, Niwa-gun (JP)

(73) Assignee: NGK INSULATORS, LTD., Nagoya (JP)

(*) Notice: Subject to any disclaimer, the term of this patent is extended or adjusted under 35 U.S.C. 154(b) by 3 days.

(21) Appl. No.: 17/038,110

(22) Filed: Sep. 30, 2020

(65) Prior Publication Data

US 2021/0102927 A1 Apr. 8, 2021

(30) Foreign Application Priority Data

Oct. 3, 2019 (JP) .............................. JP2019-183076

(51) Int. Cl.
*G01N 33/00* (2006.01)
*G01N 27/407* (2006.01)

(52) U.S. Cl.
CPC ..... *G01N 33/0009* (2013.01); *G01N 27/4077* (2013.01)

(58) Field of Classification Search
CPC ....................... G01N 27/4077; G01N 33/0009
USPC ....................................................... 73/31.05
See application file for complete search history.

(56) References Cited

U.S. PATENT DOCUMENTS

| | | | | |
|---|---|---|---|---|
| 7,708,869 B2 * | 5/2010 | Yamada | ............. | G01N 27/4071 73/23.32 |
| 2008/0156644 A1 | 7/2008 | Suzuki et al. | | |
| 2015/0101394 A1 * | 4/2015 | Fujita | ................. | G01N 27/4077 73/23.31 |
| 2016/0076919 A1 * | 3/2016 | Murakami | ........... | G01D 11/245 73/431 |
| 2017/0363596 A1 * | 12/2017 | Adachi | ............. | G01N 27/4077 |
| 2019/0285596 A1 | 9/2019 | Tanaka et al. | | |

FOREIGN PATENT DOCUMENTS

| | | |
|---|---|---|
| JP | 2008-164411 A | 7/2008 |
| JP | 2015-099142 A | 5/2015 |
| JP | 2009-158615 A | 9/2019 |

OTHER PUBLICATIONS

Unexamined U.S. Appl. No. 17/038,099, filed Sep. 30, 2020.
Unexamined U.S. Appl. No. 17/038,103, filed Sep. 30, 2020.
Unexamined U.S. Appl. No. 17/038,109, filed Sep. 30, 2020.

* cited by examiner

*Primary Examiner* — Nimeshkumar D Patel
*Assistant Examiner* — Jean F Morello
(74) *Attorney, Agent, or Firm* — Mattingly & Malur, PC

(57) ABSTRACT

A gas sensor includes a sensor element, an inner protective cover having inside a sensor element chamber and having an element chamber inlet and an element chamber outlet, and an outer protective cover having an outer inlet and an outer outlet. On a side in a downward direction with respect to the element chamber inlet, a minimum distance between the inner protective cover and the sensor element is 2.64 mm or greater. When imaginary light parallel to an axial direction of the outer outlet is irradiated from an outside of the outer protective cover to the outer outlet, the imaginary light does not reach the sensor element chamber. A minimum flow channel width of an outlet-side gas flow channel that is formed as a space between the outer protective cover and the inner protective cover is 0.67 mm or greater and 2.60 mm or less.

8 Claims, 8 Drawing Sheets

GAS SENSOR

The present application claims priority of Japanese Patent Application No. 2019-183076 filed on Oct. 3, 2019, the entire contents of which are incorporated herein by reference.

BACKGROUND OF THE INVENTION

1. Field of the Invention

The present invention relates to a gas sensor.

2. Description of the Related Art

Hitherto, a gas sensor that detects the concentration of predetermined gas, such as NOx and oxygen, in measurement-object gas, such as exhaust gas of an automobile, is known. The gas sensor includes, for example, a sensor element, an inner protective cover having a sensor element chamber in which the sensor element is placed and having an element chamber inlet and an element chamber outlet, and an outer protective cover having an outer inlet and an outer outlet. Measurement-object gas reaches the sensor element chamber from the outside of the gas sensor through the outer inlet and the element chamber inlet, and is partially introduced into the sensor element. Measurement-object gas having reached the sensor element chamber is emitted to the outside through the element chamber outlet and the outer outlet thereafter.

Incidentally, since the gas sensor is used at a temperature (for example, 850° C.) at which the sensor element is activated, when the sensor element is exposed to water, a crack may occur in the sensor element from thermal shock. For this reason, it has been studied to suppress exposure of the sensor element to water. For example, in Patent Literature 1, element chamber inlets are disposed at a side portion of an inner protective cover so as not to overlap outer inlets in an axial direction, and element chamber outlets are disposed not at a bottom portion of the inner protective cover but at the side portion such that the bottom portion of the inner protective cover and an outer outlet overlap in an axial direction, with the result that direct entry of water from the outside of a gas sensor into a sensor element chamber is prevented.

CITATION LIST

Patent Literature

PTL 1: Japanese Unexamined Patent Application Publication No. 2015-099142

SUMMARY OF THE INVENTION

However, in PTL 1, when water is present between the inner protective cover and an outer protective cover, it is inconvenient that such water is easy to enter the sensor element chamber. When water has entered the sensor element chamber, it is inconvenient that a sensor element is easily exposed to water.

The present invention is made to solve such inconvenience, and it is a main object to suppress exposure of a sensor element to water.

The present invention employs the following manner to achieve the above-described main object.

A gas sensor of the present invention includes:

a sensor element having a gas inlet port that introduces measurement-object gas and capable of detecting a specific gas concentration of the measurement-object gas having flowed in from the gas inlet port;

a cylindrical inner protective cover having inside a sensor element chamber in which a tip end of the sensor element and the gas inlet port are disposed, and having one or more element chamber inlets that are inlets to the sensor element chamber and one or more element chamber outlets that are outlets from the sensor element chamber; and a cylindrical outer protective cover disposed outside the inner protective cover and having one or more outer inlets that are inlets for the measurement-object gas from an outside and one or more outer outlets that are outlets for the measurement-object gas to the outside, wherein the outer protective cover and the inner protective cover form, as spaces between the outer protective cover and the inner protective cover, an inlet-side gas flow channel that functions as a flow channel for the measurement-object gas between the one or more outer inlets and the one or more element chamber inlets and an outlet-side gas flow channel that functions as a flow channel for the measurement-object gas between the one or more outer outlets and the one or more element chamber outlets and that does not directly communicate with the inlet-side gas flow channel, where a cross section parallel to a width direction of the sensor element along a central axis of the sensor element is a width-direction cross section, a direction parallel to an axial direction of the inner protective cover from a rear end of the sensor element toward the tip end of the sensor element is a downward direction, and a direction from the tip end of the sensor element toward the rear end of the sensor element is an upward direction, a minimum distance XW in the width-direction cross section between the sensor element and a portion of the inner protective cover on a side in the downward direction with respect to the one or more element chamber inlets is greater than or equal to 2.64 mm, and the one or more element chamber outlets and the one or more outer outlets are disposed in such a positional relation that, when imaginary light parallel to an axial direction of the outer outlet is irradiated from the outside of the outer protective cover to the outer outlet, the imaginary light does not reach an inside of the sensor element chamber, and a minimum flow channel width Y of the outlet-side gas flow channel is greater than or equal to 0.67 mm and less than or equal to 2.60 mm.

With this gas sensor, since the minimum distance XW between the inner protective cover and the sensor element on the side in the downward direction (on the side in a tip end direction) with respect to the one or more element chamber inlets is greater than or equal to 2.64 mm, even when water enters the sensor element chamber, the sensor element is less likely to be exposed to water. The reason is inferred as follows. Water having entered the sensor element chamber flows in the downward direction, so water tends to accumulate in a portion of the inner protective cover on the side in the downward direction with respect to the one or more element chamber inlets, and there are concerns that accumulated water flies off toward the sensor element because of vibrations, spontaneous flow of gas, or the like. When the minimum distance XW is greater than or equal to 2.64 mm, the gap between the sensor element and the portion of the inner protective cover on the side in the downward direction with respect to the one or more element chamber inlets widens, so, even when water accumulated in the inner protective cover flies off, the water is less likely to reach the sensor element. With this gas sensor, the one or more element chamber outlets and the one or more outer outlets are disposed in such a positional relation that, when imaginary light parallel to the axial direction of the outer outlet is irradiated from the outside of the outer protective cover to the outer outlet, the imaginary light does not reach the inside of the sensor element chamber. For this reason, it is possible to suppress direct entry of water from the one or more outer outlets of the gas sensor to the sensor element chamber. In addition, with this gas sensor, since the minimum flow channel width Y of the outlet-side gas flow channel is greater than or equal to 0.67 mm, water drained from the sensor element chamber to the outlet-side gas flow channel through the one or more element chamber outlets is easy to reach the one or more outer outlets. For this reason, water is easy to be drained to the outside of the gas sensor. In addition, since the minimum flow channel width Y of the outlet-side gas flow channel is less than or equal to 2.60 mm, even when water enters the outlet-side gas flow channel from the outside of the gas sensor to the outlet-side gas flow channel through the one or more outer outlets, the water is less likely to reach the one or more element chamber outlets. For this reason, water is less likely to enter the sensor element chamber from the one or more outer outlets. With the above configuration, the gas sensor of the present invention is capable of suppressing exposure of the sensor element to water. The term "minimum flow channel width Y" means a flow channel width in a plane having the narrowest flow channel width (also referred to as narrow width plane) among planes that are surrounded by at least one of the outer protective cover and the inner protective cover and through which measurement-object gas that flows from the one or more element chamber outlets to the one or more outer outlets definitely passes. The narrow width plane is, for example, an annular plane sandwiched by the outer protective cover and the inner protective cover. The narrow width plane may be a single plane or may be two or more planes present continuously or discretely. The phrase "the minimum flow channel width Y is greater than or equal to 0.67 mm and less than or equal to 2.60 mm" may be translated into the phrase "the diameter of a largest sphere that can reach the outer outlet from the element chamber outlet is greater than or equal to 0.67 mm and less than or equal to 2.60 mm".

In the gas sensor of the present invention, the inner protective cover may include a cylindrical first portion, a second portion provided on a side in the downward direction with respect to the first portion and on a side in the downward direction with respect to the one or more element chamber inlets and smaller in inside diameter than the first portion, and a stepped portion connecting the first portion and the second portion. Water tends to accumulate on the stepped portion; however, when the above-described minimum distance XW is greater than or equal to 2.64 mm, the distance between the stepped portion and the sensor element is at least greater than or equal to 2.64 mm, so, even when water accumulated on the stepped portion flies off, the water is difficult to reach the sensor element. For this reason, even when the inner protective cover has the stepped portion, it is possible to suppress exposure of the sensor element to water. The gas sensor of the present invention may have one or more step structures each made up of the first portion, the second portion, and the stepped portion. When a plurality of the step structures is provided, the first portion of one of the adjacent step structures may be the second portion of the other one of the adjacent step structures. In the gas sensor having the one or more step structures, it is preferable that, of the stepped portions, at least the stepped portion closest in distance to the sensor element, preferably, all the stepped portions, are disposed on the side in the downward direction with respect to a tip end surface of the sensor element. When, for example, the gas sensor is used at an angle with respect to a vertical direction, water tends to accumulate near a connection portion with the first portion larger in inside diameter than the second portion in the stepped portion; however, when the stepped portion is disposed not on a side in the upward direction but on the side in the downward direction with respect to the tip end surface of the sensor element, the distance between the connection portion and the sensor element increases, so it is possible to further suppress exposure of the sensor element to water.

In the gas sensor of the present invention, the inner protective cover may include a bottomed cylindrical tip end portion, and the one or more element chamber outlets may be disposed not at a bottom portion of the tip end portion but at a side portion of the tip end portion. When the one or more element chamber outlets are disposed not at the bottom portion but at the side portion, even when gas spontaneously flows in from the outside of the one or more element chamber outlets, the flow of gas is less likely to concentrate in a direction toward the sensor element, so it is possible to suppress a situation in which water reaches the sensor element over gas flow. In the thus configured gas sensor, the one or more outer outlets may be disposed at a bottom portion of the outer protective cover. When the one or more outer outlets are disposed at the bottom portion while the one or more element chamber outlets are disposed at the side portion, it is possible to further suppress entry of water from the outside of the gas sensor into the sensor element chamber.

In the gas sensor of the present invention, the minimum distance XW may be greater than or equal to 2.80 mm. With this configuration, even when water enters the sensor element chamber from the one or more element chamber inlets, the sensor element is further less likely to be exposed to water.

In the gas sensor of the present invention, the minimum flow channel width Y may be greater than or equal to 0.80 mm and less than or equal to 2.00 mm. When the minimum flow channel width Y of the outlet-side gas flow channel is greater than or equal to 0.80 mm, water drained from the sensor element chamber further tends to be drained to the outside of the gas sensor. When the minimum flow channel width Y of the outlet-side gas flow channel is less than or equal to 2.00 mm, even when water enters from the outside of the gas sensor through the one or more outer outlets, the water is further less likely to reach the one or more element chamber outlets.

In the gas sensor of the present invention, the inner protective cover may have a first member and a second member, the first member and the second member may form the one or more element chamber inlets as a gap between the first member and the second member, and, in each of the one or more element chamber inlets, an element-side opening that is an opening adjacent to the sensor element chamber may be open in the downward direction. With this configuration, since measurement-object gas flows in the downward direction from the one or more element chamber inlets isolated from the sensor element by the first member into the sensor element chamber, even when water is contained in measurement-object gas, the water is less likely to reach the sensor element. Here, the phrase "the element-side opening is open in the downward direction" includes a case where the one or more element chamber inlets are open parallel to the downward direction and a case where the one or more element chamber inlets are open at an angle with respect to the downward direction so as to approach the sensor element toward a lower side.

In the gas sensor of the present invention, the first member may have a first cylinder portion surrounding the sensor element, the second member may have a second cylinder portion larger in diameter than the first cylinder portion, and the one or more element chamber inlets may be a cylindrical gap between an outer peripheral surface of the first cylinder portion and an inner peripheral surface of the second cylinder portion.

DETAILED DESCRIPTION OF THE INVENTION

Figure 1:
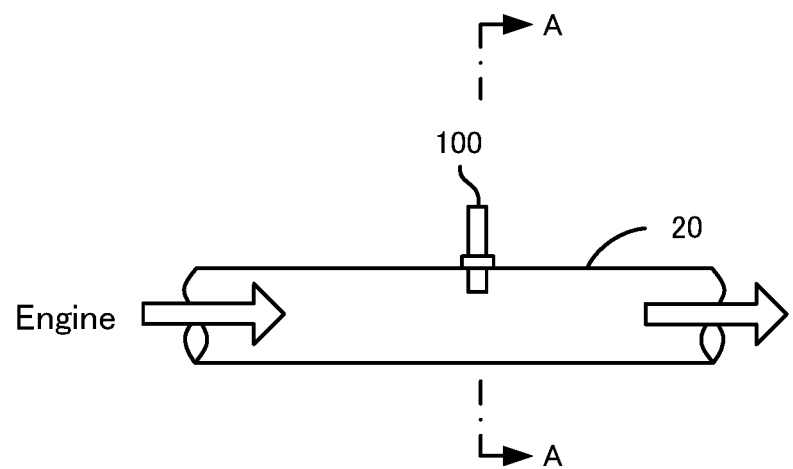
FIG. 1 is a schematic diagram of a state where a gas sensor 100 is attached to a pipe 20.
Figure 2:
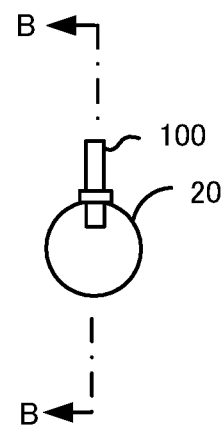
FIG. 2 is a cross-sectional view taken along the line A-A in FIG. 1.
Figure 3:
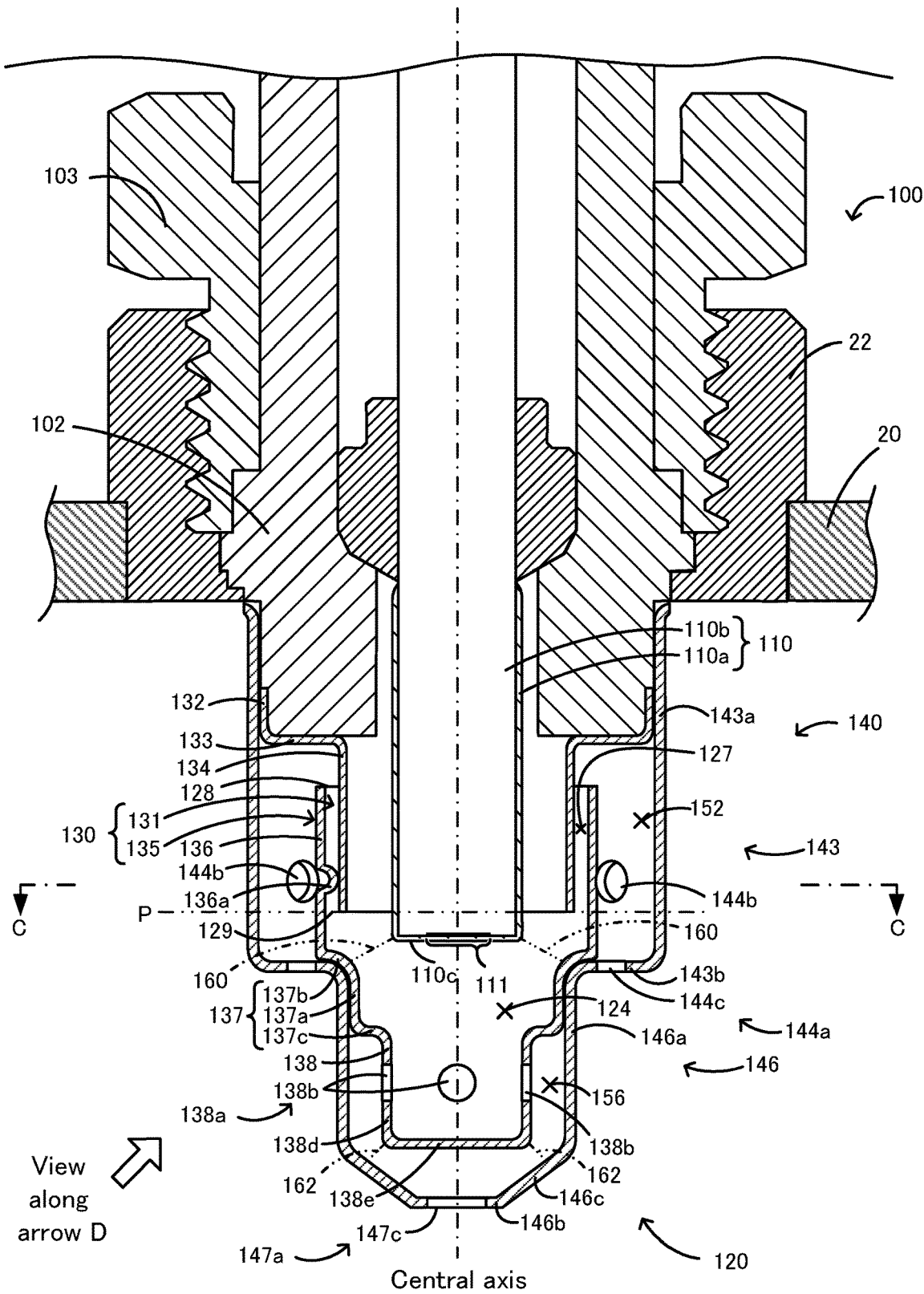
FIG. 3 is a cross-sectional view taken along the line B-B in FIG. 2.
Figure 4:
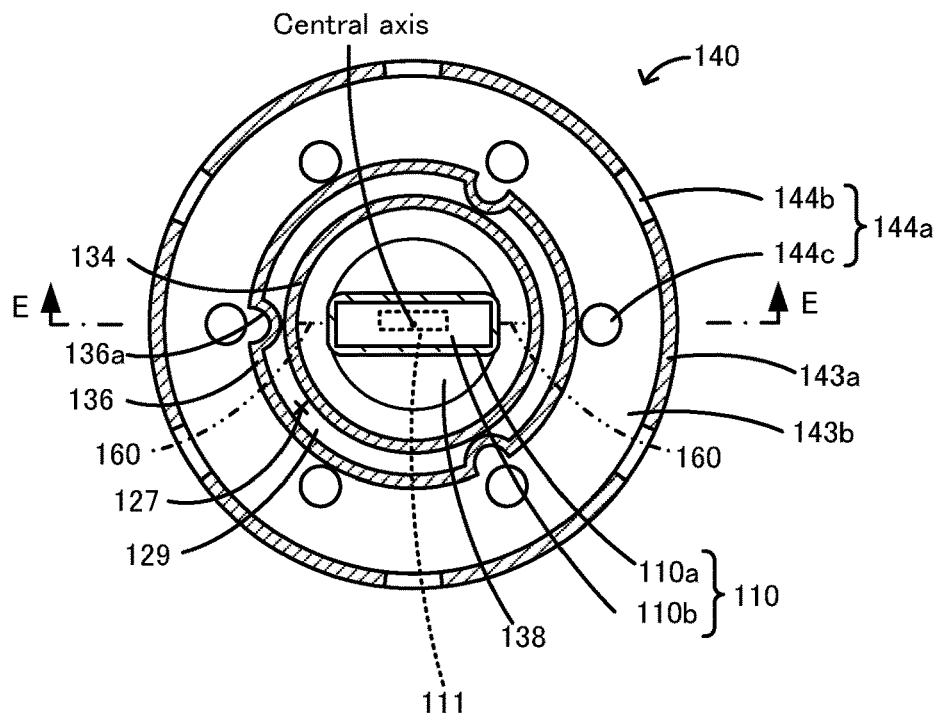
FIG. 4 is a cross-sectional view taken along the line C-C in FIG. 3.
Figure 5:
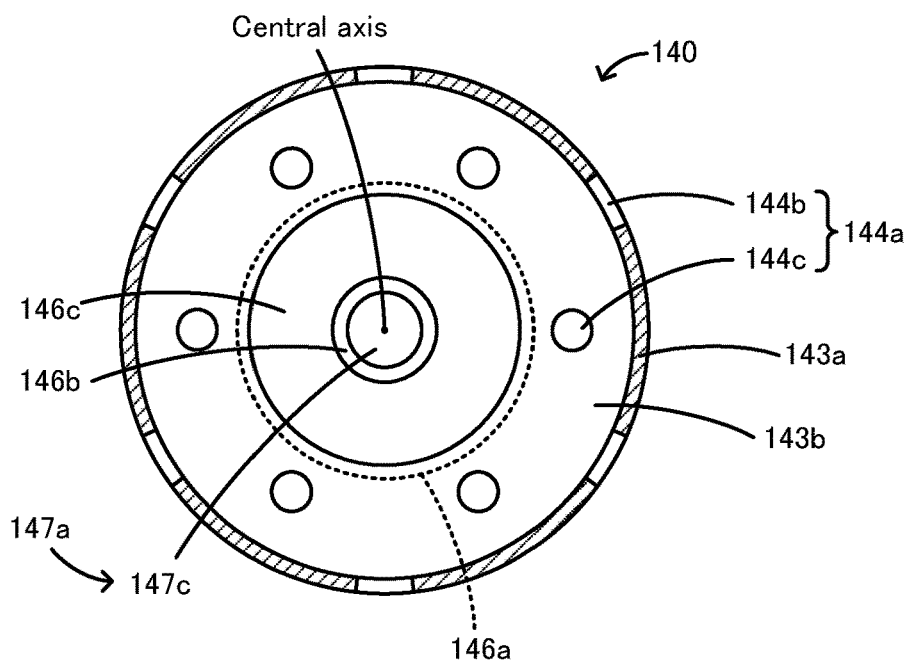
FIG. 5 is a cross-sectional view of an outer protective cover 140, taken along the line C-C in FIG. 3.
Figure 6:
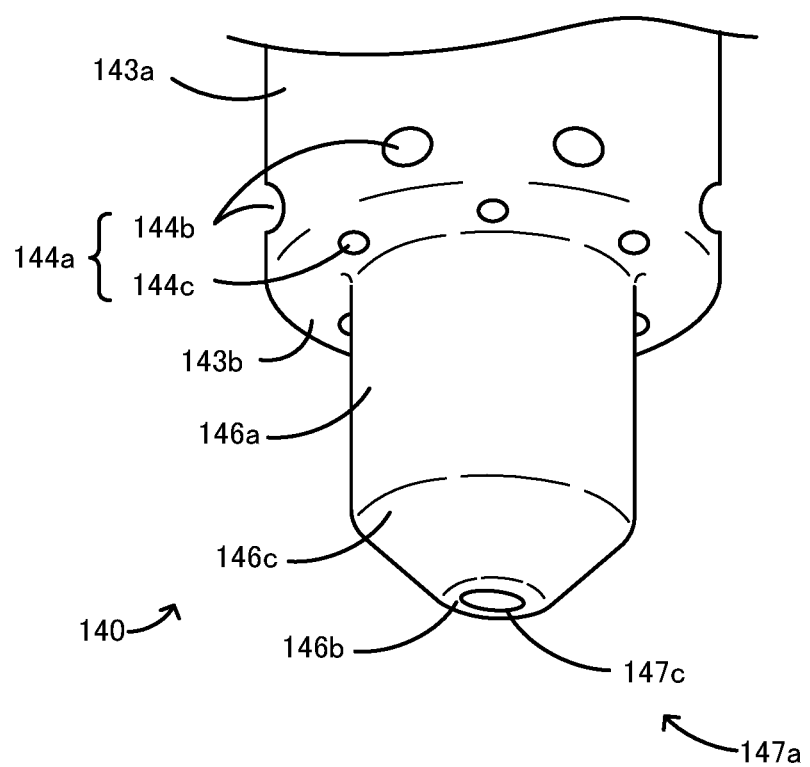
FIG. 6 is a view along the arrow D in FIG. 3.
Figure 7:
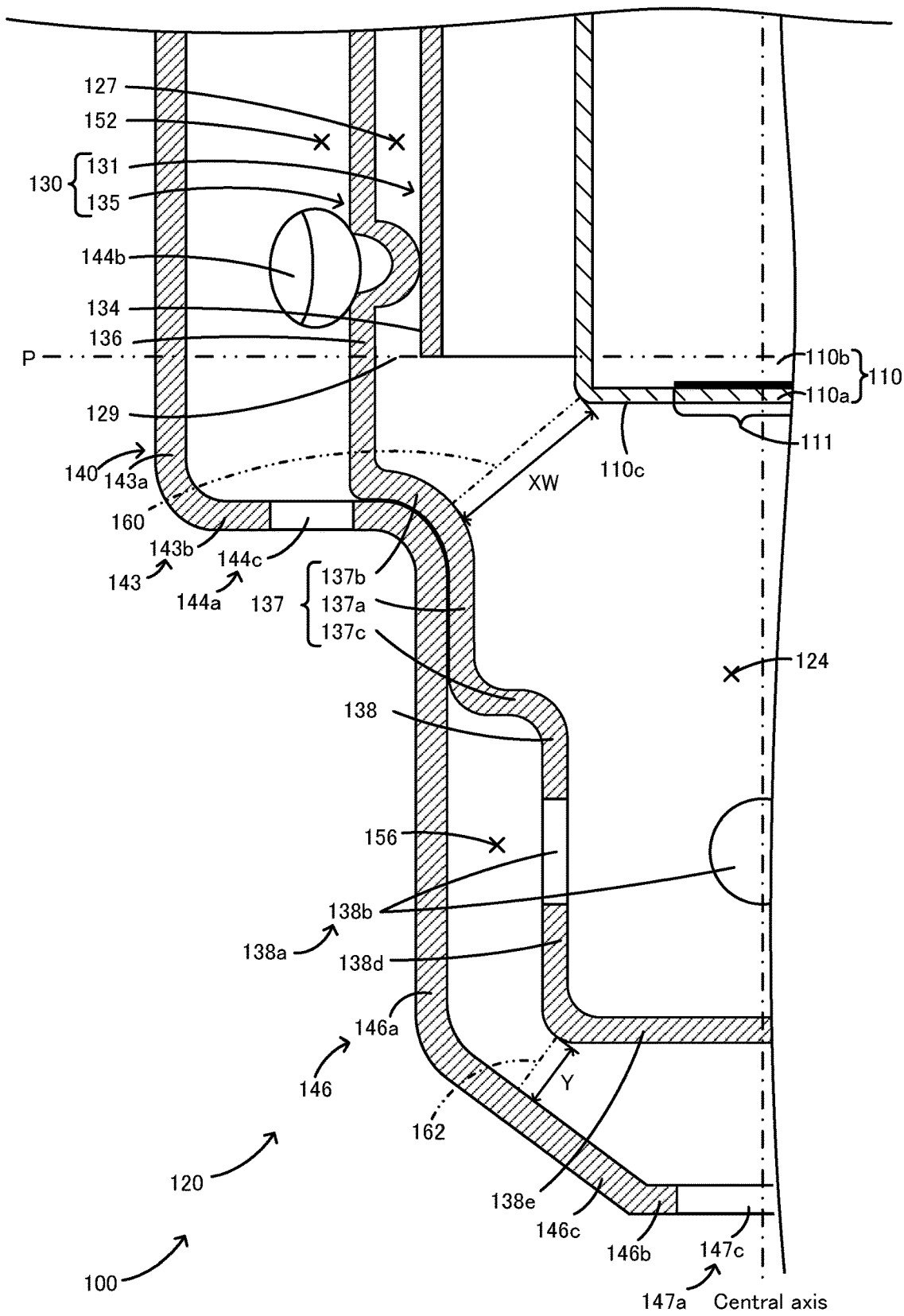
FIG. 7 is a partially enlarged view of FIG. 3.

Next, an embodiment of the present invention will be described with reference to the drawings. FIG. 1 is a schematic diagram of a state where a gas sensor 100 is attached to a pipe 20. FIG. 2 is a cross-sectional view taken along the line A-A in FIG. 1. FIG. 3 is a cross-sectional view taken along the line B-B in FIG. 2. FIG. 4 is a cross-sectional view taken along the line C-C in FIG. 3. FIG. 5 is a cross-sectional view of an outer protective cover 140, taken along the line C-C in FIG. 3. FIG. 5 corresponds to a diagram excluding a first cylinder portion 134, a second cylinder portion 136, a tip end portion 138, and a sensor element 110 from FIG. 4. FIG. 6 is a view along the arrow D in FIG. 3. FIG. 7 is a partially enlarged view of FIG. 3. A direction parallel to an axial direction of a protective cover 120 from a tip end of the sensor element 110 toward a rear end of the sensor element 110 (upward direction in FIG. 3 and FIG. 7) is defined as upward direction, and a direction parallel to the axial direction of the protective cover 120 from the rear end of the sensor element 110 toward the tip end of the sensor element 110 (downward direction in FIG. 3 and FIG. 7) is defined as downward direction.

As shown in FIG. 1, the gas sensor 100 is attached inside the pipe 20 that is an exhaust pathway from an engine of a vehicle and is configured to detect a specific gas concentration that is the concentration of at least any one specific gas of gas components, such as NOx, ammonia, and $O_2$, contained in exhaust gas as measurement-object gas emitted from the engine. As shown in FIG. 2, the gas sensor 100 is fixed to the pipe 20 in a state where a central axis of the gas sensor 100 is perpendicular to the flow of measurement-object gas in the pipe 20. The gas sensor 100 may be fixed to the pipe 20 in a state where the central axis of the gas sensor 100 is perpendicular to the flow of measurement-object gas in the pipe 20 and inclined at a predetermined angle (for example, any angle included in the range of 45° to 80°) with respect to a vertical direction.

As shown in FIG. 3, the gas sensor 100 includes the sensor element 110 having a function to detect a specific gas concentration (the concentration of NOx, ammonia, $O_2$, or the like) in measurement-object gas, and the protective cover 120 that protects the sensor element 110. The gas sensor 100 includes a metal housing 102 and a metal bolt 103 provided with external thread on its outer peripheral surface. The housing 102 is inserted in a fixing member 22 welded to the pipe 20 and provided with internal thread on its inner peripheral surface, and the housing 102 is fixed in the fixing member 22 by further inserting the bolt 103 into the fixing member 22. Thus, the gas sensor 100 is fixed to the pipe 20. A direction in which measurement-object gas flows inside the pipe 20 is a direction from the left toward the right in FIG. 3.

The sensor element 110 is an element having a narrow long planar shape and has an element body 110b with such a structure that a plurality of oxygen-ion-conductive solid electrolyte layers made of zirconia ($ZrO_2$) or the like is laminated. The element body 110b has a gas inlet port 111 that introduces therein measurement-object gas and is configured to be capable of detecting a specific gas concentration of measurement-object gas having flowed in from the gas inlet port 111. In the present embodiment, the gas inlet port 111 is open at the tip end surface of the element body 110b (the lower surface of the element body 110b in FIG. 3). The sensor element 110 includes inside a heater that plays a role in temperature adjustment to retain temperature by heating the sensor element 110. The structure of the sensor element 110 and the principle of detecting a specific gas concentration are known and are described in, for example, Japanese Unexamined Patent Application Publication No. 2008-164411. The tip end (the lower end in FIG. 3) and gas inlet port 111 of the sensor element 110 are disposed inside the sensor element chamber 124. A direction from the rear end of the sensor element 110 toward the tip end of the sensor element 110 (downward direction) is also referred to as tip end direction.

The sensor element 110 includes a porous protective layer 110a that covers at least part of the surface of the element body 110b. In the present embodiment, the porous protective layer 110a is formed on five surfaces out of six surfaces of the element body 110b and covers almost all the surface exposed to the inside of the sensor element chamber 124. Specifically, the porous protective layer 110a covers the entire tip end surface (lower surface) at which the gas inlet port 111 is formed in the element body 110b. The porous protective layer 110a covers a side closer to the tip end surface of the element body 110b on the four surfaces (the upper, lower, right, and left surfaces of the element body 110b in FIG. 4) connected to the tip end surface of the element body 110b. The lower end surface of the porous protective layer 110a is a tip end surface 110c of the sensor element 110. The porous protective layer 110a plays a role in, for example, suppressing occurrence of crack in the element body 110b as a result of adhesion of moisture or the like in measurement-object gas. The porous protective layer 110a also plays a role in suppressing adhesion of an oil component and the like contained in measurement-object gas to an electrode (not shown) or the like of the surface of the element body 110b. The porous protective layer 110a is made of, for example, a porous material, such as alumina porous material, zirconia porous material, spinel porous material, cordierite porous material, titania porous material, and magnesia porous material. The porous protective layer 110a may be formed by, for example, plasma spraying, screen printing, dipping, or the like. The porous protective layer 110a also covers the gas inlet port 111; however, since the porous protective layer 110a is a porous material, measurement-object gas is able to flow through the inside of the porous protective layer 110a and reach the gas inlet port 111. The thickness of the porous protective layer 110a is, for example, 100 μm to 700 μm.

The protective cover 120 is disposed so as to surround the sensor element 110. The protective cover 120 has a bottomed cylindrical inner protective cover 130 that covers the tip end of the sensor element 110 and a bottomed outer protective cover 140 that covers the inner protective cover 130. An inlet-side gas flow channel 152 and an outlet-side gas flow channel 156 are formed as spaces surrounded by the inner protective cover 130 and the outer protective cover 140, and a sensor element chamber 124 is formed as a space surrounded by the inner protective cover 130. The central axes of the gas sensor 100, the sensor element 110, the inner protective cover 130, and the outer protective cover 140 are coaxial with one another. The protective cover 120 is made of metal (for example, stainless steel, such as SUS310S).

The inner protective cover 130 includes a first member 131 and a second member 135. The first member 131 has a cylindrical large-diameter portion 132, a cylindrical first cylinder portion 134 smaller in diameter than the large-diameter portion 132, and a stepped portion 133 that connects the large-diameter portion 132 and the first cylinder portion 134. The first cylinder portion 134 surrounds the sensor element 110. The second member 135 has a second cylinder portion 136 larger in diameter than the first cylinder portion 134, a bottomed cylindrical tip end portion 138 located on a side in the tip end direction (downward direction) of the sensor element 110 with respect to the second cylinder portion 136, and a connection portion 137 connecting the lower end of the second cylinder portion 136 and the tip end portion 138. The connection portion 137 has a third cylinder portion 137a smaller in diameter than the second cylinder portion 136 and larger in diameter than the tip end portion 138, a first stepped portion 137b connecting the second cylinder portion 136 and the third cylinder portion 137a, and a second stepped portion 137c connecting the third cylinder portion 137a and the tip end portion 138. The first stepped portion 137b and the second stepped portion 137c both are disposed on a side in the downward direction with respect to the tip end surface 110c of the sensor element 110. The tip end portion 138 has a side portion 138d and a bottom portion 138e. The tip end portion 138 has one or more element chamber outlets 138a that communicate with the sensor element chamber 124 and the outlet-side gas flow channel 156 and that are outlets for measurement-object gas from the sensor element chamber 124. The element chamber outlets 138a include a plurality of (four in the present embodiment) horizontal holes 138b formed at equal intervals at the side portion 138d. The element chamber outlets 138a are not disposed at the bottom portion 138e of the tip end portion 138. The diameter of each element chamber outlet 138a is, for example, 0.5 mm to 2.6 mm. In the present embodiment, the diameter of each of the plurality of horizontal holes 138b is set to the same value. The element chamber outlets 138a are formed on a side in the tip end direction (downward direction) of the sensor element 110 with respect to the gas inlet port 111. In other words, the element chamber outlets 138a are located away (in the downward direction) from the gas inlet port 111 when viewed from the rear end of the sensor element 110 (the upper end (not shown) of the sensor element 110 in FIG. 3).

The large-diameter portion 132, the first cylinder portion 134, the second cylinder portion 136, and the tip end portion 138 have the same central axis. The inner peripheral surface of the large-diameter portion 132 is in contact with the housing 102. Thus, the first member 131 is fixed to the housing 102. In the second member 135, the first stepped portion 137b is in contact with the stepped portion 143b of the outer protective cover 140 and is fixed to the stepped portion 143b by welding or the like. The second member 135 may be fixed by forming the outside diameter of the tip end side (lower end side) of the third cylinder portion 137a so as to be slightly larger than the inside diameter of the tip end portion 146 of the outer protective cover 140 and press-fitting the tip end portion of the third cylinder portion 137a into the tip end portion 146.

A plurality of protruding portions 136a that protrude toward the outer peripheral surface of the first cylinder portion 134 and that are in contact with the outer peripheral surface are formed on the inner peripheral surface of the second cylinder portion 136. As shown in FIG. 4, three protruding portions 136a are provided and are disposed equally on the inner peripheral surface of the second cylinder portion 136 along the circumferential direction. Each protruding portion 136a is formed in a substantially semi-spherical shape. With the thus configured protruding portions 136a, the positional relation between the first cylinder portion 134 and the second cylinder portion 136 is easily fixed by the protruding portions 136a. It is desirable that the protruding portions 136a press the outer peripheral surface of the first cylinder portion 134 radially inward. With this configuration, it is possible to further reliably fix the positional relation between the first cylinder portion 134 and the second cylinder portion 136 with the protruding portions 136a. The number of the protruding portions 136a is not limited to three and may be two or may be more than or equal to four. Because fixing of the first cylinder portion 134 to the second cylinder portion 136 tends to be stable, it is desirable that the number of the protruding portions 136a be more than or equal to three.

The inner protective cover 130 forms an element chamber inlet 127 (see FIG. 3, FIG. 4, and FIG. 7) that is a gap between the first member 131 and the second member 135 and that is an inlet for measurement-object gas into the sensor element chamber 124. More specifically, the element chamber inlet 127 is formed as a cylindrical gap (gas flow channel) between the outer peripheral surface of the first cylinder portion 134 and the inner peripheral surface of the second cylinder portion 136. The element chamber inlet 127 has an outer opening 128 that is an opening adjacent to the inlet-side gas flow channel 152 that is a space in which the outer inlets 144a are disposed, and an element-side opening 129 that is an opening adjacent to the sensor element chamber 124 that is a space in which the gas inlet port 111 is disposed. The outer opening 128 is formed on the rear end side (upper side) of the sensor element 110 with respect to the element-side opening 129. Therefore, in the pathway of measurement-object gas from the outer inlets 144a to the gas inlet port 111, the element chamber inlet 127 is a flow channel from the rear end side (upper side) of the sensor element 110 toward the tip end side (lower side). The element chamber inlet 127 is a flow channel parallel to a rear end-tip end direction (a flow channel parallel to the up-down direction) of the sensor element 110.

The element-side opening 129 is open in a direction from the rear end of the sensor element 110 toward the tip end of the sensor element 110 (downward direction) and is open parallel to the rear end-tip end direction (up-down direction) of the sensor element 110. In other words, the element-side opening 129 is open parallel to the downward direction. Therefore, the sensor element 110 is disposed at a position other than a region that is an imaginary extension of the element chamber inlet 127 from the element-side opening 129 (a region just below the element-side opening 129 in FIG. 3 and FIG. 7). Thus, it is possible to reduce a situation in which measurement-object gas having flowed out from the element-side opening 129 directly strikes the surface of the sensor element 110 and to reduce a situation in which water reaches the sensor element 110 over gas flow.

The inner protective cover 130 is disposed such that, in the width-direction cross section parallel to the width direction of the sensor element 110 along the central axis of the sensor element 110, the minimum distance XW between the sensor element 110 and the portion that is on the side in the downward direction (on the side in the tip end direction) with respect to the element chamber inlet 127 is greater than or equal to 2.64 mm. In the present embodiment, the distance (the length of an imaginary line 160 shown in FIG. 7) between the third cylinder portion 137a-side end of the first stepped portion 137b and the tip end-side edge of the sensor element 110 is the minimum distance XW, and the inner protective cover 130 is disposed such that the minimum distance XW is greater than or equal to 2.64 mm. In the present embodiment, in the sensor element 110, a cross section perpendicular to the central axis is a rectangular shape as shown in FIG. 4, the direction of the long side of the rectangular shape is the width direction, and the direction of the short side is a thickness direction. In other words, the width-direction cross section corresponds to the E-E cross section of FIG. 4, and, in FIG. 3 and FIG. 7 showing the E-E cross section, the cross section in the width direction, obtained by dividing the sensor element 110 into two in the thickness direction along the central axis, appears. The portion on the side in the downward direction with respect to the element chamber inlet 127 means a portion on the side in the downward direction with respect to an imaginary plane P including the element-side opening 129 that is the lower end of the element chamber inlet 127, and does not include a portion in the imaginary plane P. Therefore, the portion on the side in the downward direction with respect to the element chamber inlet 127 does not include the first member 131.

As shown in FIG. 3, the outer protective cover 140 has a cylindrical body portion 143 and a bottomed cylindrical tip end portion 146 smaller in inside diameter than the body portion 143. The body portion 143 has a side portion 143a having a side surface along a central axis direction (up-down direction) of the outer protective cover 140, and a stepped portion 143b that is a bottom portion of the body portion 143 and that connects the side portion 143a and the tip end portion 146. The central axes of the body portion 143 and the tip end portion 146 all are the same as the central axis of the inner protective cover 130. A portion around the upper end in the body portion 143 is in contact with the housing 102 and the large-diameter portion 132 on its inner peripheral surface. Thus, the outer protective cover 140 is fixed to the housing 102. The body portion 143 is located so as to cover the outer circumference of the large-diameter portion 132, the first cylinder portion 134, and the second cylinder portion 136. The tip end portion 146 is located so as to cover the tip end portion 138, and the inner peripheral surface is in contact with the outer peripheral surface of the third cylinder portion 137a. The tip end portion 146 has a side portion 146a having a side surface along the central axis direction (up-down direction) of the outer protective cover 140 and of which the outside diameter is smaller than the inside diameter of the side portion 143a, a bottom portion 146b that is the bottom portion of the outer protective cover 140, and a tapered portion 146c that connects the side portion 146a and the bottom portion 146b and that reduces in diameter from the side portion 146a toward the bottom portion 146b. The tip end portion 146 is located on the side in the tip end direction (on the lower side) with respect to the body portion 143. The outer protective cover 140 has one or more (in the present embodiment, multiple and, specifically, 12) outer inlets 144a that are formed in the body portion 143 and that are inlets for measurement-object gas from the outside, and one or more outer outlets 147a that are formed in the tip end portion 146 and that are outlets for measurement-object gas to the outside.

The outer inlets 144a are holes that communicate with the outer side (outside) of the outer protective cover 140 and the inlet-side gas flow channel 152. The outer inlets 144a include a plurality of (in the present embodiment, six) horizontal holes 144b formed at equal intervals in the side portion 143a, and a plurality of (in the present embodiment, six) vertical holes 144c formed at equal intervals in the stepped portion 143b (see FIG. 3 to FIG. 6). The outer inlets 144a (horizontal holes 144b and vertical holes 144c) are holes perforated in a circular shape. The diameter of each of the 12 outer inlets 144a is, for example, 0.5 mm to 2 mm. The diameter of each outer inlet 144a may be less than or equal to 1.5 mm. In the present embodiment, the diameter of each of the plurality of horizontal holes 144b is the same value, and the diameter of each of the plurality of vertical holes 144c is the same value. The diameter of each horizontal hole 144b is greater than the diameter of each vertical hole 144c. As shown in FIG. 4 and FIG. 5, the outer inlets 144a are formed such that the horizontal holes 144b and the vertical holes 144c are alternately located at equal intervals along the circumferential direction of the outer protective cover 140. In other words, an angle formed between a line connecting the center of each horizontal hole 144b and the central axis of the outer protective cover 140 and a line connecting the center of the vertical hole 144c adjacent to that horizontal hole 144b and the central axis of the outer protective cover 140 in FIG. 4 and FIG. 5 is 30° (360°/12).

The outer outlets 147a are holes that communicate with the outer side (outside) of the outer protective cover 140 and the outlet-side gas flow channel 156. The outer outlets 147a include one or more (in the present embodiment, one) vertical holes 147c formed at the center of the bottom portion 146b of the tip end portion 146 (see FIG. 3, FIG. 5, and FIG. 6). The outer outlet 147a (here, the vertical hole 147c) is a hole perforated in a circular shape. The diameter of the outer outlet 147a is, for example, 0.5 mm to 2.5 mm. The diameter of the outer outlet 147a may be less than or equal to 1.5 mm. In the present embodiment, the diameter of the vertical hole 147c is set to a value greater than the diameter of the horizontal hole 144b or the vertical hole 144c. The outer outlet 147a is disposed by adjusting the positional relation with the element chamber outlet 138a such that, when imaginary light parallel to the axial direction of the outer outlet 147a from the outside of the outer protective cover 140 to the outer outlet 147a, the imaginary light does not reach the inside of the sensor element chamber 124. In the present embodiment, since the above-described imaginary light strikes the bottom portion 138e of the inner protective cover 130, the imaginary light does not reach the inside of the sensor element chamber 124. In the present embodiment, the outer outlet 147a is disposed not at the side portion 146a but at the bottom portion 146b such that the outer outlet 147a and the element chamber outlet 138a are open in different directions. The outer outlet 147a, different from the outer inlets 144a, is not disposed at the side portion of the outer protective cover 140 (here, the side portion 146a of the tip end portion 146). In the present embodiment, the element chamber outlet 138a is disposed not at the bottom portion 138e but at the side portion 138d so as to deviate from a region where the above-described imaginary light strikes.

The outer protective cover 140 and the inner protective cover 130 form the inlet-side gas flow channel 152 as a space between the body portion 143 and the inner protective cover 130. More specifically, the inlet-side gas flow channel 152 is a space surrounded by the stepped portion 133, the first cylinder portion 134, the second cylinder portion 136, the side portion 143a, and the stepped portion 143b. The inlet-side gas flow channel 152 functions as a flow channel for measurement-object gas between the outer inlets 144a and the element chamber inlet 127. The outer protective cover 140 and the inner protective cover 130 form the outlet-side gas flow channel 156 as a space between the tip end portion 146 and the inner protective cover 130. More specifically, the outlet-side gas flow channel 156 is a space surrounded by the tip end portion 138, the second stepped portion 137c, and the tip end portion 146. Since the inner peripheral surface of the tip end portion 146 is in contact with the outer peripheral surface of the connection portion 137, the inlet-side gas flow channel 152 and the outlet-side gas flow channel 156 do not directly communicate with each other. The outlet-side gas flow channel 156 functions as a flow channel for measurement-object gas between the outer outlet 147a and the element chamber outlets 138a. The outer protective cover 140 and the inner protective cover 130 are disposed such that the minimum flow channel width Y of the outlet-side gas flow channel 156 is greater than or equal to 0.67 mm and less than or equal to 2.60 mm. In other words, the outer protective cover 140 and the inner protective cover 130 are disposed such that the diameter of a largest sphere that is able to reach the outer outlet 147a from the element chamber outlets 138a is greater than or equal to 0.67 mm and less than or equal to 2.60 mm. In the present embodiment, the outer protective cover 140 and the inner protective cover 130 are disposed such that the width (for example, the length of a line that appears in FIG. 3 and FIG. 7) of an imaginary annular plane 162 having a truncated cone side surface between the outer periphery of the bottom portion 138e of the tip end portion 138 of the inner protective cover 130 and a portion facing the outer periphery of the bottom portion 138e in the tapered portion 146c of the outer protective cover 140 is the minimum flow channel width Y and the minimum flow channel width Y is greater than or equal to 0.67 mm and less than or equal to 2.60 mm. The element chamber outlets 138a and the outer outlet 147a may have a diameter larger than or equal to the minimum flow channel width Y or a diameter larger than the minimum flow channel width Y.

Here, the flow of measurement-object gas inside the protective cover 120 at the time when the gas sensor 100 detects a specific gas concentration will be described. Measurement-object gas that flows in the pipe 20 initially passes through at least any one of the plurality of outer inlets 144a (the horizontal holes 144b and the vertical holes 144c) and flows into the inlet-side gas flow channel 152. Subsequently, measurement-object gas flows from the inlet-side gas flow channel 152 into the element chamber inlet 127 via the outer opening 128, passes through the element chamber inlet 127, flows out from the element-side opening 129, and flows into the sensor element chamber 124. Measurement-object gas having flowed from the element-side opening 129 into the sensor element chamber 124 at least partially reaches the gas inlet port 111 of the sensor element 110. When measurement-object gas reaches the gas inlet port 111 and flows into the inside of the sensor element 110, the sensor element 110 generates an electrical signal (voltage or current) according to a specific gas concentration in the measurement-object gas, and the specific gas concentration is detected based on the electrical signal. Measurement-object gas in the sensor element chamber 124 flows into the outlet-side gas flow channel 156 through at least any one of the element chamber outlets 138a (here, the horizontal holes 138b) and flows out from there to the outside through the outer outlet 147a (here, the vertical hole 147c). The output of a heater inside the sensor element 110 is controlled by a controller (not shown) such that the sensor element 110 is maintained at a predetermined temperature.

Incidentally, condensed water may be produced inside the pipe 20 through which exhaust gas or the like of an automobile flows. Such condensed water may enter the inside of the outer protective cover 140 from the outer inlets 144a or the outer outlet 147a as a result of flow of the above-described measurement-object gas, spontaneous gas flow at engine startup, or the like and further enter the sensor element chamber 124 from the element chamber inlet 127 or the element chamber outlets 138a. Water having entered the sensor element chamber 124 flows in the downward direction under its own weight, so water tends to accumulate in an area on the side in the downward direction with respect to the element chamber inlet 127 in the inner protective cover 130. There are concerns that water accumulated in the inner protective cover 130 flies off toward the sensor element 110 by spontaneous gas flow at engine startup, vibrations, or the like. In the above-described gas sensor 100, on the side in the downward direction (tip end direction) with respect to the element chamber inlet 127, the minimum distance XW between the inner protective cover 130 and the sensor element 110 is set so as to be greater than or equal to 2.64 mm. In the present embodiment, since the sensor element 110 has a rectangular shape in cross section perpendicular to the central axis, when the minimum distance XW in the width-direction cross section is greater than or equal to 2.64 mm, a minimum distance (also referred to as minimum distance XH) between the sensor element 110 and a portion on the side in the downward direction with respect to the element chamber inlet 127 in a thickness-direction cross section (cross section perpendicular to the E-E cross section in FIG. 4 along the central axis of the sensor element 110) is greater than 2.64 mm. With the thus configured gas sensor 100, the gap between the sensor element 110 and the portion on the side in the downward direction with respect to the element chamber inlet 127 in the inner protective cover 130 is wide. Therefore, even when water accumulated in the inner protective cover 130 flies off, the water is less likely to reach the sensor element 110. With this gas sensor 100, the element chamber outlets 138a and the outer outlet 147a are disposed in such a positional relation that, when imaginary light parallel to the axial direction of the outer outlet 147a is irradiated from the outside of the outer protective cover 140 to the outer outlet 147a, the imaginary light does not reach the inside of the sensor element chamber 124. For this reason, it is possible to reduce direct entry of water from the outer outlet 147a of the gas sensor 100 to the sensor element chamber 124. In addition, with this gas sensor 100, since the minimum flow channel width Y of the outlet-side gas flow channel 156 is greater than or equal to 0.67 mm, water drained from the sensor element chamber 124 to the outlet-side gas flow channel 156 through the element chamber outlets 138a is easy to reach the outer outlet 147a side. For this reason, water tends to be drained to the outside of the gas sensor 100. In addition, since the minimum flow channel width Y of the outlet-side gas flow channel 156 is less than or equal to 2.60 mm, even when water enters the outlet-side gas flow channel 156 from the outside of the gas sensor 100 through the outer outlet 147a, the water is less likely to reach the element chamber outlets 138a. For this reason, water is less likely to enter the sensor element chamber 124 from the outer outlet 147a. With the above configuration, the gas sensor 100 of the present embodiment is capable of reducing exposure of the sensor element 110 to water. It is desirable that the minimum distance XW be greater than or equal to 2.80 mm. It is desirable that the minimum flow channel width Y be greater than or equal to 0.80 mm and less than or equal to 2.00 mm.

With this gas sensor 100, the inner protective cover 130 has a step structure made up of the cylindrical second cylinder portion 136, the third cylinder portion 137a (which corresponds to the second portion when the second cylinder portion 136 is regarded as the first portion of the present invention), and the first stepped portion 137b (which corresponds to the stepped portion when the second cylinder portion 136 is regarded as the first portion of the present invention) connecting the second cylinder portion 136 and the third cylinder portion 137a. The inner protective cover 130 also has a step structure made up of the cylindrical third cylinder portion 137a, the side portion 138d (which corresponds to the second portion when the third cylinder portion 137a is regarded as the first portion of the present invention), and the second stepped portion 137c (which corresponds to the stepped portion when the third cylinder portion 137a is regarded as the first portion of the present invention) connecting the third cylinder portion 137a and the side portion 138d. Incidentally, water tends to accumulate on the stepped portion. The gas sensor 100 of the present embodiment has two stepped portions, that is, the first stepped portion 137b and the second stepped portion 137c; however, the minimum distance between the first stepped portion 137b and the sensor element 110 is set to the above-described minimum distance XW, and the minimum distance XW is set to greater than or equal to 2.64 mm. With this configuration, since the distance between the first stepped portion 137b or the second stepped portion 137c and the sensor element 110 is greater than or equal to at least 2.64 mm, even when water accumulated on the first stepped portion 137b or the second stepped portion 137c flies off, the water is less likely to reach the sensor element 110. A gas sensor is mostly used in a state where the central axis is inclined with respect to the vertical direction, and, in that case, water tends to accumulate near the connection portion with the first portion in the stepped portions. Therefore, the first stepped portion 137b and the second stepped portion 137c are disposed not on the side in the upward direction but on the side in the downward direction with respect to the tip end surface 110c of the sensor element 110 such that the distance between the connection portion and the sensor element 110 increases. For this reason, exposure of the sensor element 110 to water is further suppressed.

With the gas sensor 100 of the present embodiment described in detail above, the minimum distance XW between the inner protective cover 130 and the sensor element 110 is greater than or equal to 2.64 mm on the side in the downward direction with respect to the element chamber inlet 127. The element chamber outlets 138a and the outer outlet 147a are disposed in such a positional relation that, when imaginary light parallel to the axial direction of the outer outlet 147a is irradiated from the outside of the outer protective cover 140 to the outer outlet 147a, the imaginary light does not reach the inside of the sensor element chamber 124. In addition, the minimum flow channel width Y of the outlet-side gas flow channel 156 is greater than or equal to 0.67 mm and less than or equal to 2.60 mm. For this reason, exposure of the sensor element 110 to water is suppressed.

The element chamber outlets 138a are disposed not at the bottom portion 138e of the tip end portion 138 but at the side portion 138d. Therefore, even when gas spontaneously flows in from the outside of the element chamber outlets 138a, flow of gas is less likely to concentrate in the direction toward the sensor element 110, and water is less likely to reach the sensor element 110 over gas flow. Not only the element chamber outlets 138a are disposed at the side portion 138d but also the outer outlet 147a is disposed at the bottom portion 146b of the outer protective cover 140. Therefore, water is further less likely to enter the sensor element chamber 124 from the outside of the gas sensor 100.

In addition, when the minimum distance XW is greater than or equal to 2.80 mm, even when water enters the sensor element chamber 124 from the element chamber inlet 127, the sensor element 110 is further less likely to be exposed to water. When the minimum flow channel width Y is greater than or equal to 0.80 mm, water drained from the sensor element chamber 124 tends to be drained to the outside of the gas sensor 100. When the minimum flow channel width Y is less than or equal to 2.00 mm, even when water enters from the outside of the gas sensor 100 through the outer outlet 147a, the water is further less likely to reach the element chamber outlets 138a.

Furthermore, in the gas sensor 100, the first member 131 and the second member 135 form the element chamber inlet 127 such that the element-side opening 129 is open in the downward direction. With this configuration, since measurement-object gas flows downward from the element chamber inlet 127 isolated from the sensor element 110 by the first member 131 into the sensor element chamber 124, even when water is contained in measurement-object gas, the water is less likely to reach the sensor element 110.

The present invention is not limited to the above-described embodiment and may be, of course, implemented in various modes within the technical scope of the present invention.

For example, in the above-described embodiment, the inner protective cover 130 has two stepped portions (the first stepped portion 137b and the second stepped portion 137c). Alternatively, the inner protective cover 130 does not need to have a stepped portion or the number of the stepped portions may be one or three or more. For example, the second stepped portion 137c may be omitted as in the case of a gas sensor 200 of FIG. 8 (described later), or the first stepped portion 137b may be omitted as in the case of a gas sensor 400 of FIG. 10 (described later). In the above-described embodiment, the distance between the first stepped portion 137b and the sensor element 110 is set to the minimum distance XW. Alternatively, the distance between the second stepped portion 137c and the sensor element 110 may be set to the minimum distance XW, or the distance between the sensor element 110 and a portion other than the stepped portions may be set to the minimum distance XW.

In the above-described embodiment, the tip end portion 138 of the inner protective cover 130 has such a shape that the outside diameter of the side portion 138d is constant and the side portion 138d and the bottom portion 138e have the same diameters. Alternatively, the tip end portion 138 may have such a shape that the outside diameter of the side portion 138d reduces as it approaches the bottom portion 138e, for example, an inverted truncated cone shape shown in FIG. 8 (described later). In other words, the tip end portion 138 of the inner protective cover 130 may have a tapered portion.

Figure 8:
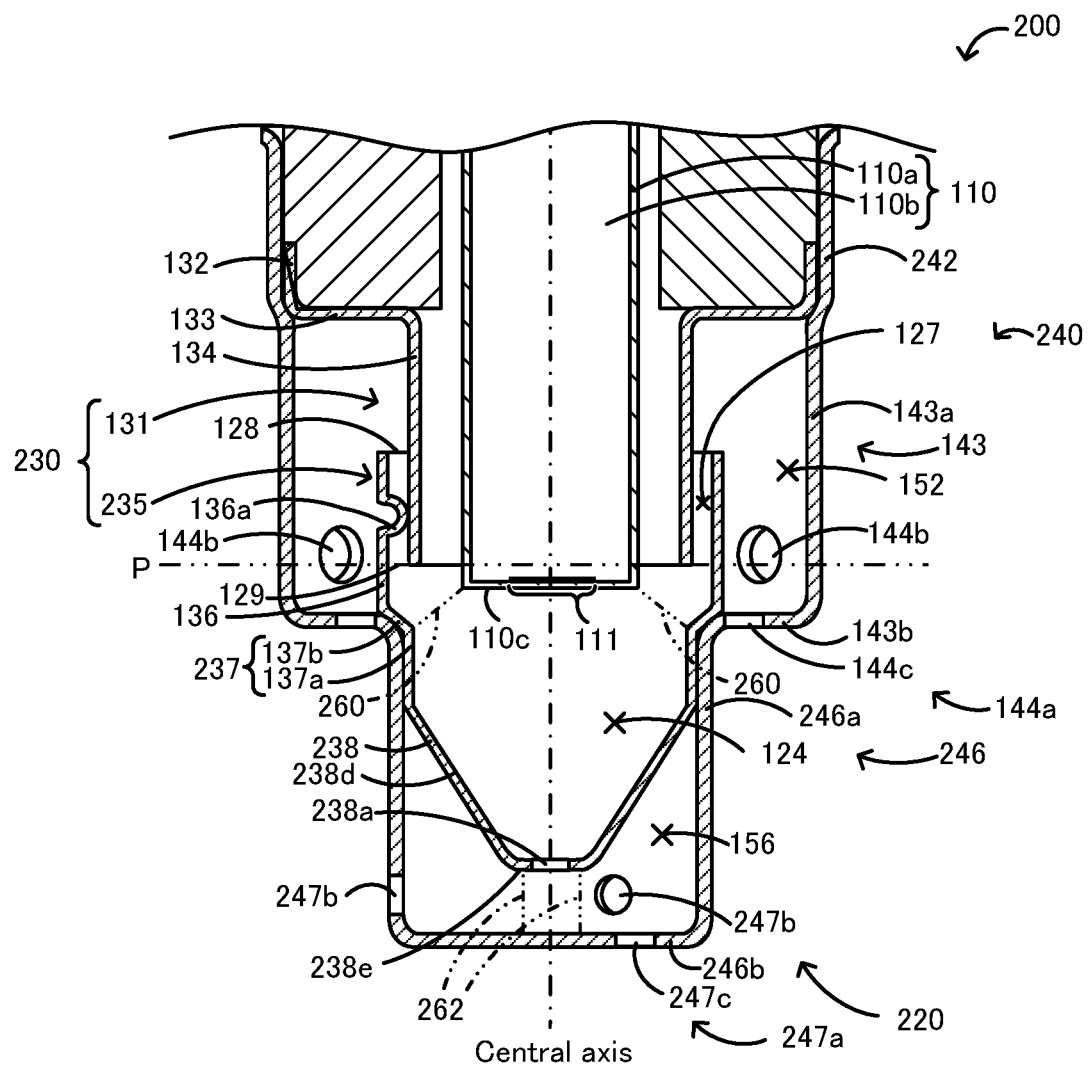
FIG. 8 is a longitudinal sectional view of a gas sensor 200 of a modification.

In the above-described embodiment, the tip end portion 146 of the outer protective cover 140 has a bottomed cylindrical shape and has the side portion 146a, the bottom portion 146b, and the tapered portion 146c. Alternatively, the tip end portion 146 may have a cylindrical shape without the tapered portion 146c as shown in FIG. 8 (described later).

In the above-described embodiment, the outer inlets 144a include the horizontal holes 144b and the vertical holes 144c. Alternatively, the outer inlets 144a may include only any one-type hole. In addition to or instead of the horizontal holes 144b and the vertical holes 144c, a corner hole may be formed at a corner portion at the boundary between the side portion 143a and the stepped portion 143b. For the element chamber outlets 138a and the outer outlet 147a as well, similarly, any one or more types of a horizontal hole, a vertical hole, and a corner hole may be formed. The outer outlets 147a may include a through-hole provided at the tapered portion 146c. For the element chamber outlets 138a as well, similarly, a through-hole provided at a tapered portion (for example, a tapered portion 238d (described later)) may be formed. The element chamber outlets 138a, the outer inlets 144a, and the outer outlet 147a each are not limited to a hole and may be a gap between a plurality of members that make up the protective cover 120 as in the case of the element chamber inlet 127, and it is sufficient that the number of each is one or more.

In the above-described embodiment, the minimum flow channel width Y is a flow channel width in the imaginary annular plane 162 having a truncated cone side surface between the outer protective cover 140 and the inner protective cover 130; however, the minimum flow channel width Y is not limited thereto. For example, the shape of the imaginary annular plane may be a disc shape or may be a cylindrical shape. The minimum flow channel width Y may be a flow channel width in a non-annular plane surrounded by only the outer protective cover 140 or only the inner protective cover 130.

In the above-described embodiment, the protruding portions 136a are formed on the inner peripheral surface of the second cylinder portion 136; however, the configuration is not limited thereto. It is sufficient that a plurality of protruding portions is formed on at least one of the outer peripheral surface of the first cylinder portion 134 and the inner peripheral surface of the second cylinder portion 136 so as to protrude toward the other surface and contact with the other surface. In the above-described embodiment, as shown in FIG. 3 and FIG. 4, the outer peripheral surfaces of portions where the protruding portions 136a are formed in the second cylinder portion 136 are recessed inward; however, the configuration is not limited thereto. Alternatively, the outer peripheral portions do not need to be recessed. The protruding portions 136a are not limited to a semi-spherical shape and may be any shape. The protruding portions 136a do not need to be formed on the outer peripheral surface of the first cylinder portion 134 or on the inner peripheral surface of the second cylinder portion 136.

FIG. 8 is a longitudinal sectional view of a gas sensor 200 of a modification. In FIG. 8, like reference signs are assigned to the same components as those of the gas sensor 100, and the detailed description thereof is omitted. As shown in FIG. 8, a protective cover 220 of the gas sensor 200 includes an inner protective cover 230 instead of the inner protective cover 130, and includes an outer protective cover 240 instead of the outer protective cover 140. A second member 235 of the inner protective cover 230 has a tip end portion 238 having an inverted truncated cone shape, and a connection portion 237 having such a shape that the second stepped portion 137c is omitted, instead of the tip end portion 138 and the connection portion 137 in FIG. 3. The tip end portion 238 has a bottom portion 238e that is the bottom portion of the inner protective cover 230, and a tapered portion 238d that reduces in diameter from the third cylinder portion 137a toward the bottom portion 238e. The tip end portion 238 has an element chamber outlet 238a that communicates with the sensor element chamber 124 and the outlet-side gas flow channel 156 and that is an outlet for measurement-object gas from the sensor element chamber 124. The element chamber outlet 238a is a single circular vertical hole formed at the center of the bottom portion 238e of the tip end portion 238. The outer protective cover 240 has a cylindrical large-diameter portion 242 larger in diameter than the body portion 143 above the body portion 143. In the outer protective cover 240, not the body portion 143 but the inner peripheral surface of the large-diameter portion 242 is in contact with the housing 102 and the large-diameter portion 132. The outer protective cover 240 has a bottomed cylindrical (cylindrical) tip end portion 246 from which the tapered portion 146c is omitted, instead of the tip end portion 146 of FIG. 3. The tip end portion 246 has a side portion 246a having a side surface along the central axis direction (up-down direction in FIG. 8) of the outer protective cover 240 and of which the outside diameter is smaller than the inside diameter of the side portion 143a, and a bottom portion 246b that is the bottom portion of the outer protective cover 240. Outer outlets 247a that are outlets for measurement-object gas to the outside are formed at the tip end portion 246. The outer outlets 247a include three horizontal holes 247b (only two are shown in FIG. 8) formed at equal intervals at the side portion 246a of the tip end portion 246 along the circumferential direction of the outer protective cover 240, and three vertical holes 247c (only one is shown in FIG. 8) formed at equal intervals at the bottom portion 246b along the circumferential direction of the outer protective cover 240. The horizontal holes 247b and the vertical holes 247c are located alternately at equal intervals along the circumferential direction of the outer protective cover 240, and an angle (phase) formed between the adjacent horizontal hole 247b and vertical hole 247c is 60°. In the gas sensor 200, as well as the gas sensor 100, the distance (the length of an imaginary line 260 shown in FIG. 8) between the third cylinder portion 137a-side end of the first stepped portion 137b and the tip end-side edge of the sensor element 110 is the minimum distance XW, and the inner protective cover 230 is disposed such that the minimum distance XW is greater than or equal to 2.64 mm. In the gas sensor 200, the positional relation between the element chamber outlet 238a and the outer outlets 247a are adjusted such that, when imaginary light parallel to the axial direction of each outer outlet 247a from the outside of the outer protective cover 240 to the outer outlet 247a, the imaginary light does not reach the inside of the sensor element chamber 124. Specifically, the element chamber outlet 238a is disposed so as to be open perpendicular to the horizontal holes 247b at the bottom portion 238e disposed on the side in the upward direction with respect to the upper end of the horizontal holes 247b so as to deviate from a region where imaginary light irradiated from the horizontal holes 247b in the outer outlets 247a strikes. The element chamber outlet 238a is disposed so as to be open in the same direction as the vertical holes 247c of the outer outlets 247a and is disposed at a position that deviates from a region extended from the vertical holes 247c in the axial direction such that imaginary light irradiated from each vertical hole 247c strikes. In the gas sensor 200, the outer protective cover 240 and the inner protective cover 230 are disposed such that the width (for example, the length of a line that appears in FIG. 8) of an imaginary annular plane 262 between an annular portion around the element chamber outlet 238a of the bottom portion 238e of the tip end portion 238 of the inner protective cover 230 and a portion facing the annular portion in the bottom portion 246b of the outer protective cover 240 is the minimum flow channel width Y and the minimum flow channel width Y is greater than or equal to 0.67 mm and less than or equal to 2.60 mm. The imaginary annular plane 262 has a cylindrical shape. With this gas sensor 200 as well, similar advantageous effects are obtained with similar characteristics of the above-described gas sensor 100. In other words, since the minimum distance XW is greater than or equal to 2.64 mm, the element chamber outlet 238a and the outer outlets 247a are disposed in the above-described positional relation, and the minimum flow channel width Y is greater than or equal to 0.67 mm and less than or equal to 2.60 mm, exposure of the sensor element 110 to water is suppressed.

Figure 9:
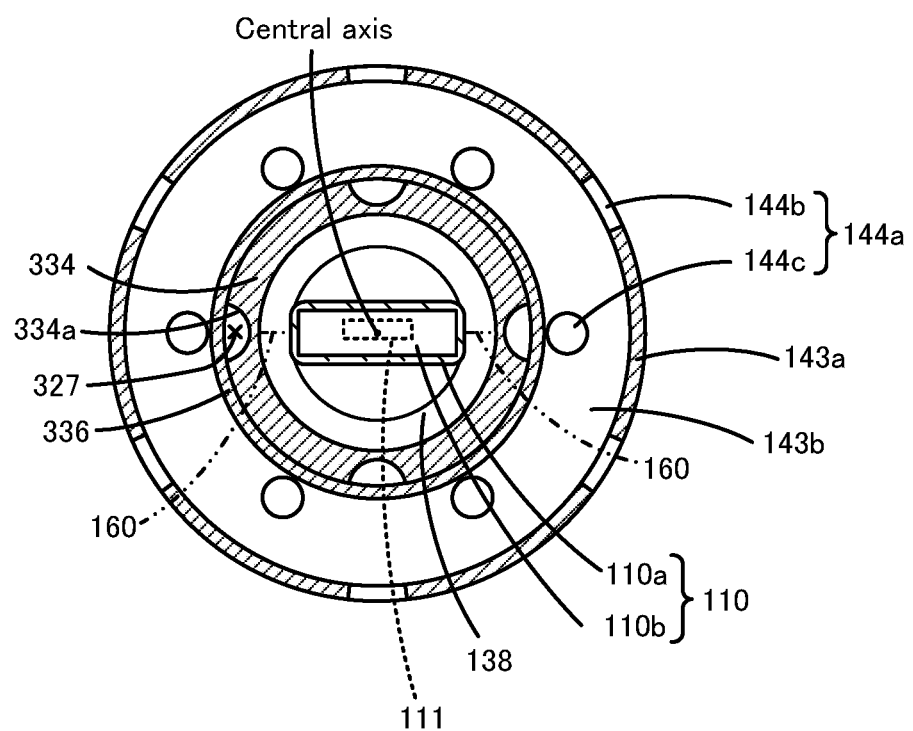
FIG. 9 is a cross-sectional view showing an element chamber inlet 327 of a modification.

In the above-described embodiment, the element chamber inlet 127 is a cylindrical gap between the outer peripheral surface of the first cylinder portion 134 and the inner peripheral surface of the second cylinder portion 136; however, the configuration is not limited thereto. For example, a recessed portion (groove) may be formed on at least one of the outer peripheral surface of the first cylinder portion and the inner peripheral surface of the second cylinder portion, and the element chamber inlet may be a gap formed by the recessed portion between the first cylinder portion and the second cylinder portion. FIG. 9 is a cross-sectional view showing an element chamber inlet 327 of a modification. In FIG. 9, like reference signs are assigned to the same components as those of the gas sensor 100, and the detailed description thereof is omitted. As shown in FIG. 9, the outer peripheral surface of the first cylinder portion 334 and the inner peripheral surface of the second cylinder portion 336 are in contact with each other, and a plurality of (four in FIG. 9) recessed portions 334a is formed at equal intervals on the outer peripheral surface of the first cylinder portion 334. The gap between the recessed portions 334a and the inner peripheral surface of the second cylinder portion 336 is the element chamber inlet 327.

Figure 10:
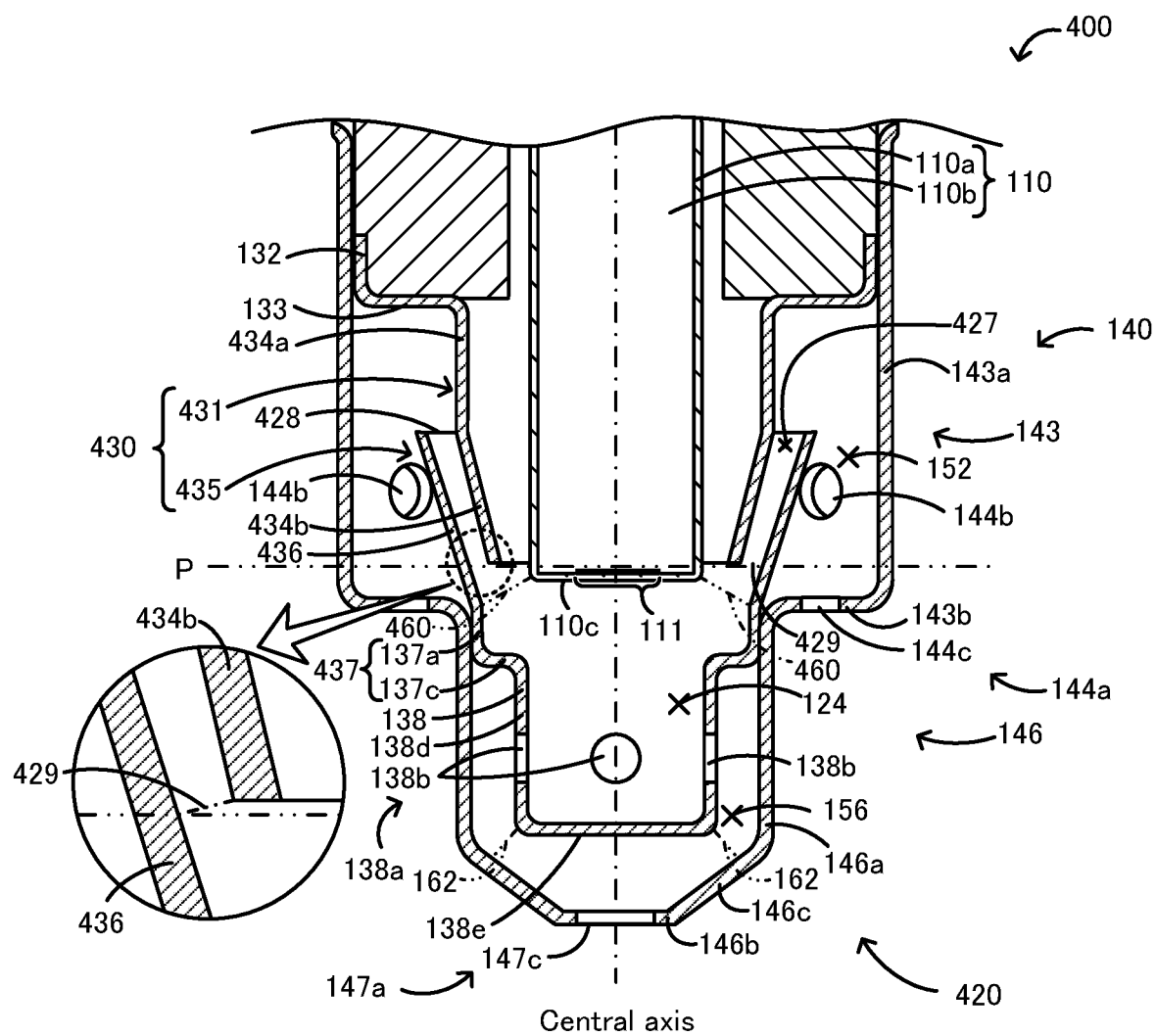
FIG. 10 is a longitudinal sectional view of a gas sensor 400 of a modification.

In the above-described embodiment, the element chamber inlet 127 is a flow channel parallel to the rear end-tip end direction of the sensor element 110 (a flow channel parallel to the up-down direction in FIG. 3). Alternatively, the element chamber inlet 127 may be a flow channel inclined at an angle with respect to the up-down direction so as to approach the sensor element 110 toward the downward side. FIG. 10 is a longitudinal sectional view of a gas sensor 400 of a modification in this case. In FIG. 10, like reference signs are assigned to the same components as those of the gas sensor 100, and the detailed description thereof is omitted. As shown in FIG. 10, a protective cover 420 of the gas sensor 400 includes an inner protective cover 430 instead of the inner protective cover 130. The inner protective cover 430 includes a first member 431 and a second member 435. The first member 431, as compared to the first member 131, includes a cylindrical body portion 434a and a cylindrical first cylinder portion 434b that reduces in diameter toward the lower side, instead of the first cylinder portion 134. The first cylinder portion 434b is connected to the body portion 434a at its upper end portion. The second member 435, as compared to the second member 135, includes a cylindrical second cylinder portion 436 that reduces in diameter toward the lower side, instead of the second cylinder portion 136, and includes a connection portion 437 from which the first stepped portion 137b is omitted, instead of the connection portion 137. The outer peripheral surface of the first cylinder portion 434b and the inner peripheral surface of the second cylinder portion 436 are not in contact with each other, and the gap formed therebetween serves as an element chamber inlet 427. The element chamber inlet 427 has an outer opening 428 that is an opening adjacent to the inlet-side gas flow channel 152 and an element-side opening 429 that is an opening adjacent to the sensor element chamber 124. The element chamber inlet 427 is a flow channel inclined at an angle with respect to the up-down direction so as to approach the sensor element 110 (so as to approach the central axis of the inner protective cover 430) toward the lower side according to the shapes of the first cylinder portion 434b and the second cylinder portion 436. Similarly, the element-side opening 429 is open at an angle with respect to the up-down direction so as to approach the sensor element 110 toward the lower side (see the enlarged view in FIG. 10). Therefore, the portion on the side in the downward direction with respect to the element chamber inlet 427 represents a portion on the side in the downward direction with respect to an imaginary plane P including the lower end of the element-side opening 429. Therefore, the portion on the side in the downward direction with respect to the element chamber inlet 427 does not include the first member 431. The orientation of the opening of the element-side opening 429 is the axial direction of the opening, which is determined based on the outer peripheral surface of the first cylinder portion 434b and the inner peripheral surface of the second cylinder portion 436 around the opening. An opening plane of the element-side opening 429 is a plane perpendicular to the axial direction of the opening. The sensor element 110 is disposed at a position other than a region that is an imaginary extension of the element chamber inlet 427 from the element-side opening 429. Thus, it is possible to reduce a situation in which measurement-object gas having flowed out from the element-side opening 429 directly strikes the surface of the sensor element 110 and to reduce a situation in which water reaches the sensor element 110 over gas flow. In the gas sensor 400, the distance (the length of the imaginary line 460 shown in FIG. 10) between the connection portion between the second cylinder portion 436 and the third cylinder portion 137a and the tip end-side edge of the sensor element 110 is the minimum distance XW, and the inner protective cover 430 and the sensor element 110 are disposed such that the minimum distance XW is greater than or equal to 2.64 mm. In the gas sensor 400, as well as the gas sensor 100, the outer protective cover 140 and the inner protective cover 430 are disposed such that the minimum flow channel width Y is greater than or equal to 0.67 mm and less than or equal to 2.60 mm. With this gas sensor 400 as well, similar advantageous effects are obtained with similar characteristics of the above-described gas sensor 100. In other words, since the minimum distance XW is greater than or equal to 2.64 mm, the element chamber outlets 138a and the outer outlets 147a are disposed in the above-described positional relation, and the minimum flow channel width Y is greater than or equal to 0.67 mm and less than or equal to 2.60 mm, exposure of the sensor element 110 to water is suppressed.

When the element chamber inlet 427 is a flow channel inclined at an angle with respect to the up-down direction or when the element-side opening 429 is open at an angle with respect to the up-down direction as in the case of the gas sensor 400 of FIG. 10, the direction of flow of measurement-object gas that flows from the element chamber inlet 427 to the sensor element chamber 124 is a direction inclined at an angle with respect to the up-down direction. Thus, similar advantageous effects to those of the element chamber inlet 127 or the element-side opening 129 of the above-described embodiment are obtained. In other words, since measurement-object gas flows downward from the element chamber inlet 427 isolated from the sensor element 110 by the first member 431 into the sensor element chamber 124, even when water is contained in measurement-object gas, the water is less likely to reach the sensor element 110. In FIG. 10, the flow channel width of the element chamber inlet 427 narrows toward the lower side of the sensor element 110. Therefore, the opening area of the element-side opening 429 is less than the opening area of the outer opening 428. Thus, when measurement-object gas flows in from the outer opening 428 and flows out from the element-side opening 429, the flow speed of measurement-object gas increases at the time of flowing out as compared to at the time of flowing in. Therefore, it is possible to improve the response of specific gas concentration detection. In FIG. 10, the element chamber inlet 427 is a flow channel inclined at an angle with respect to the up-down direction, the element-side opening 429 is open at an angle with respect to the up-down direction, and the opening area of the element-side opening 429 is less than the opening area of the outer opening 428. Alternatively, one or more of these three features may be omitted, or a gas sensor may have one or more of these three features.

In the above-described embodiment, the inner protective cover 130 includes two members, that is, the first member 131 and the second member 135. Alternatively, the first member 131 and the second member 135 may be an integrated member.

In the above-described embodiment, the sensor element 110 has a rectangular shape in cross section perpendicular to the central axis. Alternatively, the cross section perpendicular to the central axis may have a square shape or a circular shape. In this case, since the size of the sensor element 110 in the width direction and the size of the sensor element 110 in the thickness direction are equal to each other, when the minimum distance XW is greater than or equal to 2.64 mm in the width-direction cross section, the minimum distance XH is also greater than or equal to 2.64 mm.

In the above-described embodiment, the gas inlet port 111 is open at the tip end surface of the element body 110b (the lower surface of the element body 110b in FIG. 3); however, the configuration is not limited thereto. For example, the gas inlet port 111 may be open at the side surface of the element body 110b (the surface, extending in the up-down direction, of the element body 110b in FIG. 4).

In the above-described embodiment, the sensor element 110 includes the porous protective layer 110a. Alternatively, the sensor element 110 does not need to include the porous protective layer 110a. In this case, the lower surface of the element body 110b is the tip end surface of the sensor element 110.

EXAMPLES

Hereinafter, specific examples of a manufactured gas sensor will be described as examples. The present invention is not limited to the following examples.

Example 1

The gas sensor 100 shown in FIG. 3 to FIG. 7 was assumed as Example 1. In Example 1, the minimum distance XW was set to 3.24 mm, and the minimum flow channel width Y was set to 1.06 mm.

Examples 2 to 4

Example 2 was configured similarly to the gas sensor 100 of Example 1 except that the position of the sensor element 110 was moved to the side in the downward direction with respect to the protective cover 120 such that the minimum distance XW was 2.89 mm. Example 3 was configured similarly to the gas sensor 100 of Example 1 except that the position of the sensor element 110 was moved to the side in the downward direction with respect to the protective cover 120 such that the minimum distance XW was 2.64 mm and the length of the side portion 138d was extended such that the minimum flow channel width Y was 0.67 mm. Example 4 was configured similarly to the gas sensor 100 of Example 1 except that the position of the sensor element 110 was moved to the side in the downward direction with respect to the protective cover 120 such that the minimum distance XW was 2.64 mm and the length of the side portion 138d was shortened such that the minimum flow channel width Y was 2.60 mm.

Comparative Example 1

The gas sensor 200 shown in FIG. 8 was set as Comparative Example 1. In Comparative Example 1, the minimum distance XW was set to 2.64 mm, and the minimum flow channel width Y was set to 2.88 mm. In Comparative Example 1, the position of the sensor element 110 relative to the protective cover 220 was moved to the side in the downward direction as compared to FIG. 8, the first stepped portion 137b was provided on the upper side with respect to the tip end surface 110c of the sensor element 110, and the third cylinder portion 137a-side end of the first stepped portion 137b was located in an imaginary plane including the tip end surface 110c of the sensor element 110.

Comparative Examples 2 and 3

Comparative Example 2 was configured similarly to the gas sensor 100 of Example 3 except that the length of the side portion 138d was extended such that the minimum flow channel width Y was 0.48 mm. Example 3 was configured similarly to the gas sensor 100 of Example 1 except that the position of the sensor element 110 was moved in the downward direction with respect to the protective cover 120 such that the minimum distance XW was 2.46 mm.

[Evaluation of Amount of Water Exposure]

The water exposure test apparatus described in Japanese Unexamined Patent Application Publication No. 2019-158615 was used to evaluate the amount of water exposure.

The water exposure test apparatus includes a pipe having inside a flow channel for gas and disposed horizontally and linearly, a blower provided upstream of the pipe, a pressure fluctuation generator provided downstream side of the pipe, and a chamber that is part of the pipe between the blower and the pressure fluctuation generator and to which a gas sensor is attached. A vibration generator that adds vibrations to the chamber is connected to the chamber. With this water exposure test apparatus, it is possible to cause moisture to fly off toward a gas sensor by gas that simulates exhaust gas from an engine. In the water exposure test, initially, a gas sensor was placed inside the chamber of the water exposure test apparatus in a state where the central axis of the gas sensor was perpendicular to the axis of the pipe and inclined at 10° with respect to the horizontal direction. Then, a predetermined amount of moisture was supplied into the pipe between the blower and the chamber. Subsequently, gas (the atmosphere) was supplied into the pipe by using the blower, the pressure of gas was caused to fluctuate by using the pressure fluctuation generator, and vibrations were added to the chamber by the vibration generator. Thus, moisture supplied into the pipe flies off toward the gas sensor placed inside the chamber by the gas that fluctuates in pressure. In this state, a heater incorporated in a sensor element was driven to control a heater power such that the temperature of the sensor element was set to a predetermined target value between 100° C. and 200° C. The amount of water exposure of the sensor element in each gas sensor was obtained by applying a controlled value of heater power at this time to a pre-derived relationship between a heater power and an amount of water exposure. Determination was made where "A (Excellent)" was assigned for the case where the amount of water exposure was less than or equal to 10 μL, "B (Good)" was assigned for the case where the amount of water exposure was greater than 10 μL and less than or equal to 20 μL, "C (Pass)" was assigned for the case where the amount of water exposure was greater than 20 μL and less than or equal to 30 μL, and "F (Fail)" was assigned for the case where the amount of water exposure was greater than 30 μL. The results are shown in Table 1.

It is found from Table 1 that, when the minimum distance XW is greater than or equal to 2.64 mm, the outer outlet and the element chamber outlets are disposed such that the above-described imaginary light does not reach the inside of the sensor element chamber, and the minimum flow channel width Y is greater than or equal to 0.67 mm and less than or equal to 2.60 mm, the amount of water exposure is reduced to less than or equal to 30 μL. It is also found that the amount of water exposure is reduced as the minimum flow channel width Y approaches from a smaller side to near 1.06 mm and the amount of water exposure is reduced as the minimum flow channel width Y approaches from a larger side to 1.06 mm. It is also found that the amount of water exposure is reduced as the minimum distance XW increases. It is inferred from the above results that it is desirable that the minimum distance XW be greater than or equal to 2.64 mm and it is more desirable that the minimum distance XW be greater than or equal to 2.80 mm. It is also inferred that it is desirable that the minimum flow channel width Y be greater than or equal to 0.67 mm and less than or equal to 2.60 mm and it is more desirable that the minimum flow channel width Y be greater than or equal to 0.80 mm and less than or equal to 2.00 mm.

TABLE 1

| | Minimum distance XW mm | Reaching of the imaginary light into the sensor element chamber | Minimum flow channel width Y mm | Evaluation |
|---|---|---|---|---|
| Example1 | 3.24 | None | 1.06 | A |
| Example2 | 2.89 | None | 1.06 | B |
| Example3 | 2.64 | None | 0.67 | C |
| Example4 | 2.64 | None | 2.60 | C |
| Comparative Example1 | 2.64 | None | 2.88 | F |
| Comparative Example2 | 2.64 | None | 0.48 | F |
| Comparative Example3 | 2.46 | None | 1.06 | F |

What is claimed is:
1. A gas sensor comprising:
a sensor element having a gas inlet port that introduces measurement-object gas and capable of detecting a specific gas concentration of the measurement-object gas having flowed in from the gas inlet port;
a cylindrical inner protective cover having inside a sensor element chamber in which a tip end of the sensor element and the gas inlet port are disposed, and having one or more element chamber inlets that are inlets to the sensor element chamber and one or more element chamber outlets that are outlets from the sensor element chamber; and
a cylindrical outer protective cover disposed outside the inner protective cover and having one or more outer inlets that are inlets for the measurement-object gas from an outside and one or more outer outlets that are outlets for the measurement- object gas to the outside, wherein
the outer protective cover and the inner protective cover form, as spaces between the outer protective cover and the inner protective cover, an inlet-side gas flow channel that functions as a flow channel for the measurement-object gas between the one or more outer inlets and the one or more element chamber inlets and an outlet-side gas flow channel that functions as a flow channel for the measurement-object gas between the one or more outer outlets and the one or more element chamber outlets and that does not directly communicate with the inlet-side gas flow channel,
a cross section parallel to a width direction of the sensor element along a central axis of the sensor element is a width-direction cross section, a direction parallel to an axial direction of the inner protective cover from a rear end of the sensor element toward the tip end of the sensor element is a downward direction, and a direction from the tip end of the sensor element toward the rear end of the sensor element is an upward direction, a minimum distance XW in the width-direction cross section between the sensor element and a portion of the inner protective cover on a side in the downward direction with respect to the one or more element chamber inlets is greater than or equal to 2.64 mm,
the one or more element chamber outlets and the one or more outer outlets are disposed in such a positional relation that, when imaginary light passing through the one or more outer outlets is irradiated from the outside of the outer protective cover to the one or more outer outlets, the imaginary light does not directly reach the one or more element chamber outlets, and a minimum flow channel width Y of the outlet-side gas flow channel is greater than or equal to 0.67 mm and less than or equal to 2.60 mm, the inner protective cover includes a first bottomed cylindrical tip end portion, and the one or more element chamber outlets are disposed not at a bottom portion of the first bottomed cylindrical tip end portion but at a side portion of the first bottomed cylindrical tip end portion.

2. The gas sensor according to claim 1, wherein
the inner protective cover includes a cylindrical first portion, a second portion provided on a side in the downward direction with respect to the first portion and on a side in the downward direction with respect to the one or more element chamber inlets and smaller in inside diameter than the first portion, and a stepped portion connecting the first portion and the second portion.

3. The gas sensor according to claim 1, wherein
the one or more outer outlets are disposed at a bottom portion of the outer protective cover.

4. The gas sensor according to claim 1, wherein
the minimum distance XW is greater than or equal to 2.80 mm.

5. The gas sensor according to claim 1, wherein
the minimum flow channel width Y is greater than or equal to 0.80 mm and less than or equal to 2.00 mm.

6. The gas sensor according to claim 1, wherein
the inner protective cover has a first member and a second member, the first member and the second member form the one or more element chamber inlets as a gap between the first member and the second member, and in each of the one or more element chamber inlets, an element-side opening that is an opening adjacent to the sensor element chamber is open in the downward direction.

7. The gas sensor according to claim 6, wherein
the first member has a first cylinder portion surrounding the sensor element, the second member has a second cylinder portion larger in diameter than the first cylinder portion, and the one or more element chamber inlets are a cylindrical gap between an outer peripheral surface of the first cylinder portion and an inner peripheral surface of the second cylinder portion.

8. The gas sensor according to claim 1, wherein
the outer protective cover includes a second bottomed cylindrical tip end portion, and at least one of the one or more outer outlets is disposed at a center portion of the second bottomed cylindrical tip end portion.

* * * * *